United States Patent
Okuya et al.

(10) Patent No.: US 11,116,452 B2
(45) Date of Patent: Sep. 14, 2021

(54) BIOLOGICAL SIGNAL MEASUREMENT SYSTEM

(71) Applicant: Panasonic Intellectual Property Management Co., Ltd., Osaka (JP)

(72) Inventors: Teruhisa Okuya, Osaka (JP); Tomomi Nakagawa, Osaka (JP); Keita Yoshimura, Osaka (JP); Mikio Iwakawa, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 294 days.

(21) Appl. No.: 15/437,666

(22) Filed: Feb. 21, 2017

(65) Prior Publication Data
US 2017/0296126 A1 Oct. 19, 2017

(30) Foreign Application Priority Data
Apr. 14, 2016 (JP) .............................. JP2016-081482

(51) Int. Cl.
*A61B 5/00* (2006.01)
*A61B 5/026* (2006.01)
(Continued)

(52) U.S. Cl.
CPC .............. *A61B 5/7203* (2013.01); *A61B 5/01* (2013.01); *A61B 5/026* (2013.01); *A61B 5/165* (2013.01);
(Continued)

(58) Field of Classification Search
None
See application file for complete search history.

(56) References Cited

U.S. PATENT DOCUMENTS

| 4,201,224 A | * | 5/1980 | John | A61B 5/0476 600/544 |
| 4,716,907 A | * | 1/1988 | Nakamura | A61B 5/0484 600/544 |

(Continued)

FOREIGN PATENT DOCUMENTS

| JP | 2001-000407 | 1/2001 |
| JP | 2001-120511 | 5/2001 |

(Continued)

OTHER PUBLICATIONS

Office Action for corresponding Japanese Patent Application No. 2016-081482 dated Feb. 12, 2020.

*Primary Examiner* — Sean P Dougherty
*Assistant Examiner* — Benjamin S Melhus
(74) *Attorney, Agent, or Firm* — Renner, Otto, Boisselle & Sklar, LLP

(57) ABSTRACT

A biological signal measurement system includes: a biological signal measurer that measures a biological signal including external noise of biological noise and of environmental noise; biological noise measurer that measures a signal including the biological noise; a biological noise estimator that estimates the biological noise from the signal measured by the biological noise measurer; an environmental noise measurer that measures a signal including the environmental noise; an environmental noise estimator that estimates the environmental noise from the signal measured by the environmental noise measurer; and a calculator that calculates the biological signal in consideration of an effect of the external noise using the signal measured by the biological signal measurer, the biological noise estimated by the biological noise estimator and the environmental noise estimated by the environmental noise estimator.

14 Claims, 8 Drawing Sheets

(51) Int. Cl.
*A61B 5/01* (2006.01)
*A61B 5/16* (2006.01)
*A61B 5/0478* (2006.01)
*A61B 5/291* (2021.01)
*A61B 5/0205* (2006.01)
*A61B 5/369* (2021.01)

(52) U.S. Cl.
CPC ............ *A61B 5/291* (2021.01); *A61B 5/4266* (2013.01); *A61B 5/6821* (2013.01); *A61B 5/6822* (2013.01); *A61B 5/6824* (2013.01); *A61B 5/6826* (2013.01); *A61B 5/6829* (2013.01); *A61B 5/0205* (2013.01); *A61B 5/369* (2021.01); *A61B 5/6814* (2013.01); *A61B 2560/0247* (2013.01); *A61B 2562/0209* (2013.01)

(56) References Cited

U.S. PATENT DOCUMENTS

| | | | | |
|---|---|---|---|---|
| 4,781,200 A * | 11/1988 | Baker | ........... | A61B 5/02411 600/483 |
| 5,813,993 A * | 9/1998 | Kaplan | ........... | A61B 5/0476 600/544 |
| 6,544,170 B1 * | 4/2003 | Kajihara | ........... | A61B 5/04009 600/300 |
| 6,588,423 B1 * | 7/2003 | Sinderby | ........... | A61B 5/04884 128/204.23 |
| 7,286,871 B2 * | 10/2007 | Cohen | ........... | A61B 5/04004 600/300 |
| 7,502,643 B2 * | 3/2009 | Farringdon | ........... | A61B 5/0428 600/509 |
| 8,224,433 B2 * | 7/2012 | Suffin | ........... | A61B 5/4833 600/544 |
| 8,538,512 B1 * | 9/2013 | Bibian | ........... | A61B 5/04001 600/544 |
| 8,914,100 B2 * | 12/2014 | Adachi | ........... | A61B 5/048 600/544 |
| 8,989,835 B2 * | 3/2015 | Badower | ........... | A61B 5/0006 600/383 |
| 9,504,427 B2 * | 11/2016 | George | ........... | G06K 9/0051 |
| 10,226,198 B2 * | 3/2019 | Terada | ........... | A61B 5/048 |
| 10,271,754 B2 * | 4/2019 | Bahney | ........... | A61B 5/0408 |
| 2004/0260169 A1 * | 12/2004 | Sternnickel | ........... | A61B 5/7203 600/409 |
| 2005/0113703 A1 * | 5/2005 | Farringdon | ........... | A61B 5/4812 600/509 |
| 2006/0042409 A1 * | 3/2006 | Nemoto | ........... | A61B 5/4818 73/866.1 |
| 2007/0048707 A1 * | 3/2007 | Caamano | ........... | A61B 5/6814 434/236 |
| 2007/0055169 A1 * | 3/2007 | Lee | ........... | A61B 5/04012 600/544 |
| 2008/0306397 A1 * | 12/2008 | Bonmassar | ........... | A61B 5/0478 600/544 |
| 2009/0156907 A1 * | 6/2009 | Jung | ........... | A61B 6/501 600/300 |
| 2011/0118636 A1 * | 5/2011 | Kitamura | ........... | A61B 5/4818 601/84 |
| 2012/0271121 A1 | 10/2012 | Della Torre et al. | | |
| 2013/0063550 A1 * | 3/2013 | Ritchey | ........... | G06F 1/1626 348/36 |
| 2013/0331711 A1 * | 12/2013 | Mathur | ........... | A61B 5/0205 600/483 |
| 2014/0107494 A1 * | 4/2014 | Kato | ........... | A61B 5/4064 600/473 |
| 2015/0080675 A1 | 3/2015 | Shin | | |
| 2016/0019914 A1 * | 1/2016 | Sugiyama | ........... | A61B 5/7235 381/56 |
| 2016/0120434 A1 * | 5/2016 | Park | ........... | A61B 5/046 600/301 |
| 2018/0070831 A1 * | 3/2018 | Sutin | ........... | A61B 5/6814 |

FOREIGN PATENT DOCUMENTS

| | | |
|---|---|---|
| JP | 2004-154512 | 6/2004 |
| JP | 2009-189398 | 8/2009 |
| JP | 2011161021 A | 8/2011 |
| JP | 2014-505533 | 3/2014 |
| JP | 2015-054240 | 3/2015 |
| WO | WO 2012/165602 | 12/2012 |

* cited by examiner

| BIOLOGICAL INFORMATION TO BE MEASURED | BRAIN WAVES (NO NOISE INCLUDED) |
|---|---|
| BIOLOGICAL SIGNAL MEASURER | BRAIN WAVES (NOISE INCLUDED) |
| BIOLOGICAL NOISE MEASURER | MYOELECTRIC POTENTIAL OF LIVING BODY (SUCH AS SWALLOWING SPIT, MOVING NECK) |
| ENVIRONMENTAL NOISE MEASURER | MAGNETIC OR RADIO NOISE GENERATED BY PERIPHERAL EQUIPMENT |

FIG. 10

|  | A | B | C | D |
|---|---|---|---|---|
| BIOLOGICAL INFORMATION TO BE MEASURED | SYMPATHETIC NERVE ACTIVITY, PARASYMPATHETIC NERVE ACTIVITY | | | |
| BIOLOGICAL SIGNAL MEASURER | FINGERTIP TEMPERATURE | NOSE TEMPERATURE | INSTEP TEMPERATURE | FOOT FINGERTIP TEMPERATURE |
| BIOLOGICAL NOISE MEASURER | WRIST TEMPERATURE BACK OF HAND TEMPERATURE | FOREHEAD TEMPERATURE | ANKLE TEMPERATURE | ANKLE TEMPERATURE INSTEP TEMPERATURE |
| ENVIRONMENTAL NOISE MEASURER | TEMPERATURE, HUMIDITY, AIR CURRENT, RADIANT HEAT | | | |

FIG. 11

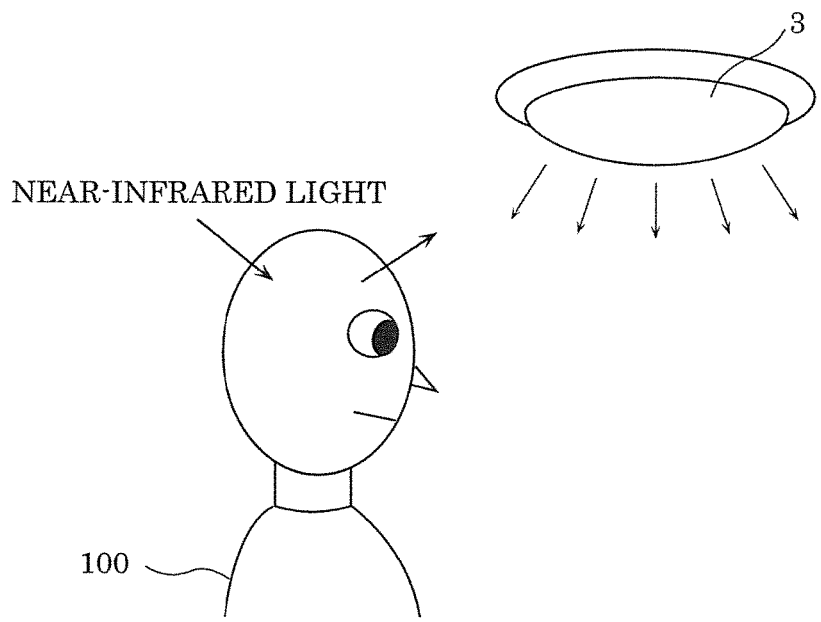

FIG. 12

| BIOLOGICAL INFORMATION TO BE MEASURED | BRAIN ACTIVITY |
|---|---|
| BIOLOGICAL SIGNAL MEASURER | CHANGE IN ABSORBANCE OF PORTION OF ATTENTION (CHANGE IN BLOOD VOLUME) |
| BIOLOGICAL NOISE MEASURER | CHANGE IN ABSORBANCE OF WHOLE BRAIN (CHANGE IN BLOOD VOLUME) |
| ENVIRONMENTAL NOISE MEASURER | CHANGE IN LIGHTING IN MEASUREMENT ENVIRONMENT CHANGE IN INCIDENCE ANGLE TO MEASURING PROBE |

| BIOLOGICAL INFORMATION TO BE MEASURED | EMOTIONAL SWEATING (NO NOISE INCLUDED) |
|---|---|
| BIOLOGICAL SIGNAL MEASURER | AMOUNT OF EMOTIONAL SWEATING (SPL) (NOISE INCLUDED) |
| BIOLOGICAL NOISE MEASURER | AMOUNT OF EMOTIONAL SWEATING DUE TO CHANGE IN BODY TEMPERATURE |
| ENVIRONMENTAL NOISE MEASURER | TEMPERATURE, WIND SPEED, RADIANT HEAT |

BIOLOGICAL SIGNAL MEASUREMENT SYSTEM

CROSS REFERENCE TO RELATED APPLICATION

This application claims the benefit of priority of Japanese Patent Application Number 2016-081482 filed on Apr. 14, 2016, the entire content of which is hereby incorporated by reference.

BACKGROUND

1. Technical Field

The present disclosure relates to a biological signal measurement system.

2. Description of the Related Art

A conventional biological signal measurement system for measuring biological signals such as brain waves is known. In this type of biological signal measurement system, in order to obtain a biological signal of a user with a high S/N ratio, a technique to reduce or remove a noise component from the measured biological signal has been proposed.

For instance, in Japanese Unexamined Patent Application Publication No. 2004-154512, a noise component is reduced from the a biological signal such as a heart-rate signal, a pulse signal or a respiration signal using a signal amplification shaper including a signal amplification circuit and a bandpass filter. Specifically, a measured biological signal is amplified by a signal amplification circuit, and only signals with frequencies (for instance, approximately 7 Hz to approximately 30 Hz) necessary for measuring the intensity of a biological signal are passed by a bandpass filter, thereby reducing noise components other than the biological signal.

SUMMARY

Using the method disclosed by Japanese Unexamined Patent Application Publication No. 2004-154512, it is possible to reduce environmental noise which is not originating from a user (subject). The environmental noise includes, for instance, a signal with approximately 1 Hz caused by wind, a signal with 50 to 60 Hz coming from a fluorescent lamp, a signal with 300 Hz or higher in sound, and low frequency noise with 20 to 300 Hz coming from a construction site or a factory.

However, external noise in various frequency bands is superimposed on a measured biological signal. Specifically, not only environmental noise which is not originating from a user, but also biological noise which is originating from a user may be superimposed on a measured biological signal. The biological noise includes, for instance, noise caused by tooth grinding of a user during measurement of a biological signal.

The present disclosure solves such a problem and it is an object to provide a biological signal measurement system capable of obtaining a biological signal with a high S/N ratio in consideration of the effect of external noise of biological noise and of environmental noise.

In order to achieve the above-mentioned object, one aspect of the present disclosure provides a biological signal measurement system including: a biological signal measurer that measures a biological signal including external noise of biological noise and of environmental noise; a biological noise measurer that measures a signal including the biological noise; a biological noise estimator that estimates the biological noise from the signal measured by the biological noise measurer; an environmental noise measurer that measures a signal including the environmental noise; an environmental noise estimator that estimates the environmental noise from the signal measured by the environmental noise measurer; and a calculator that calculates a biological signal in consideration of an effect of the external noise, using the biological signal measured by the biological signal measurer, the biological noise estimated by the biological noise estimator and the environmental noise estimated by the environmental noise estimator.

It is possible to obtain a biological signal with a high S/N ratio in consideration of the effect of the external noise of the biological noise and of the environmental noise.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 10 is a table illustrating examples of signals measured by using the biological signal measurement system according to Embodiment 2;

FIG. 11 is an illustration schematically depicting the manner in which a biological signal of a user is measured using a biological signal measurement system according to Embodiment 3;

FIG. 12 is a table illustrating examples of signals measured by using the biological signal measurement system according to Embodiment 3;

DETAILED DESCRIPTION OF THE EMBODIMENTS

Hereinafter, an embodiment of the present disclosure will be described. It is to be noted that each of the embodiments described below illustrates a specific example of the present disclosure. Therefore, the numerical values, components, arrangement positions and connection configuration of the components, steps, and order of the steps that are presented in the following embodiments are examples, which are not intended to limit the present disclosure. In the following embodiments, the components thereof, which are not recited in the independent claims that define the most generic concept of the present disclosure, are described as arbitrary structural components.

It is to be noted that the respective figures are schematic diagrams and are not necessarily precise illustrations. Furthermore, in the respective figures, the same reference sign is given to substantially identical components, and a redundant description is omitted or simplified.

Embodiment 1

Figure 1:
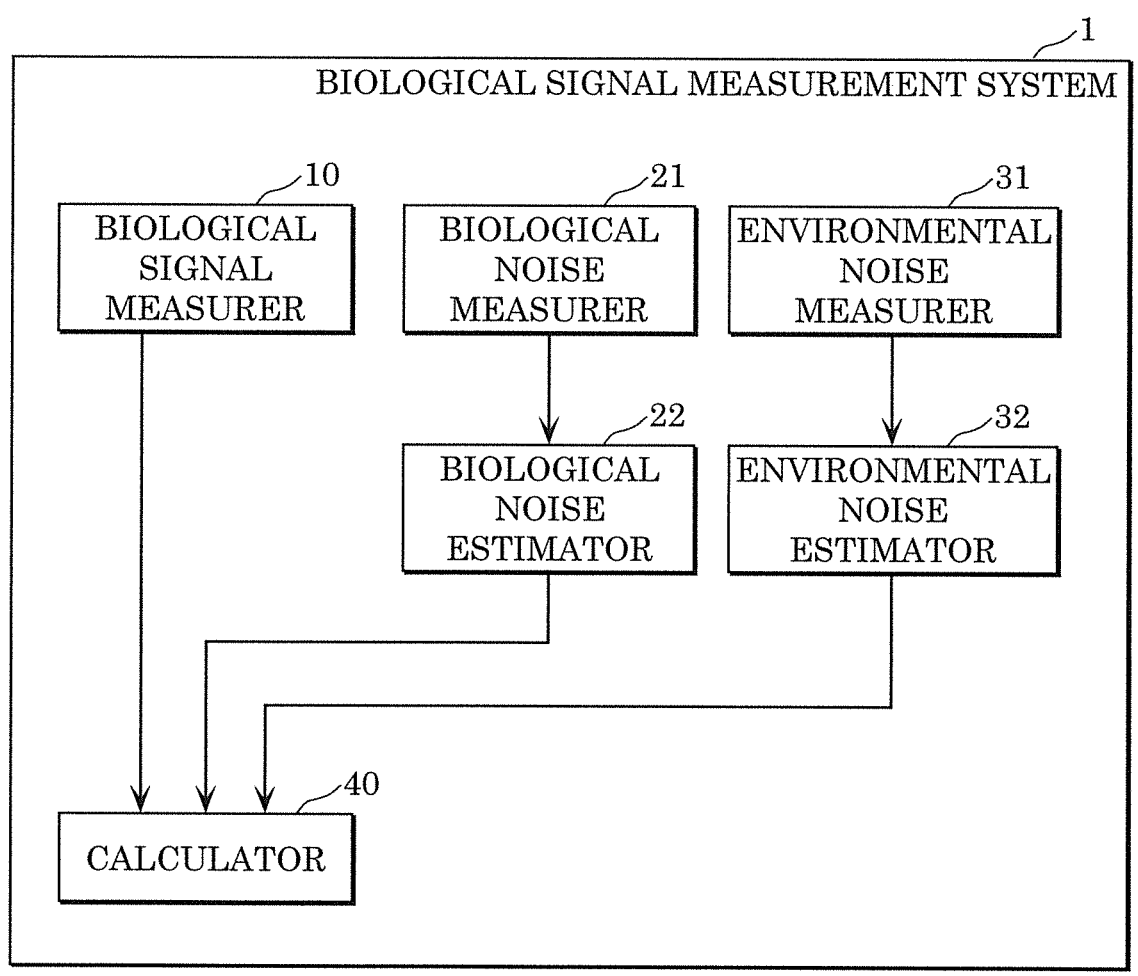
FIG. 1 is a block diagram illustrating the configuration of a biological signal measurement system according to Embodiment 1.
Figure 2:
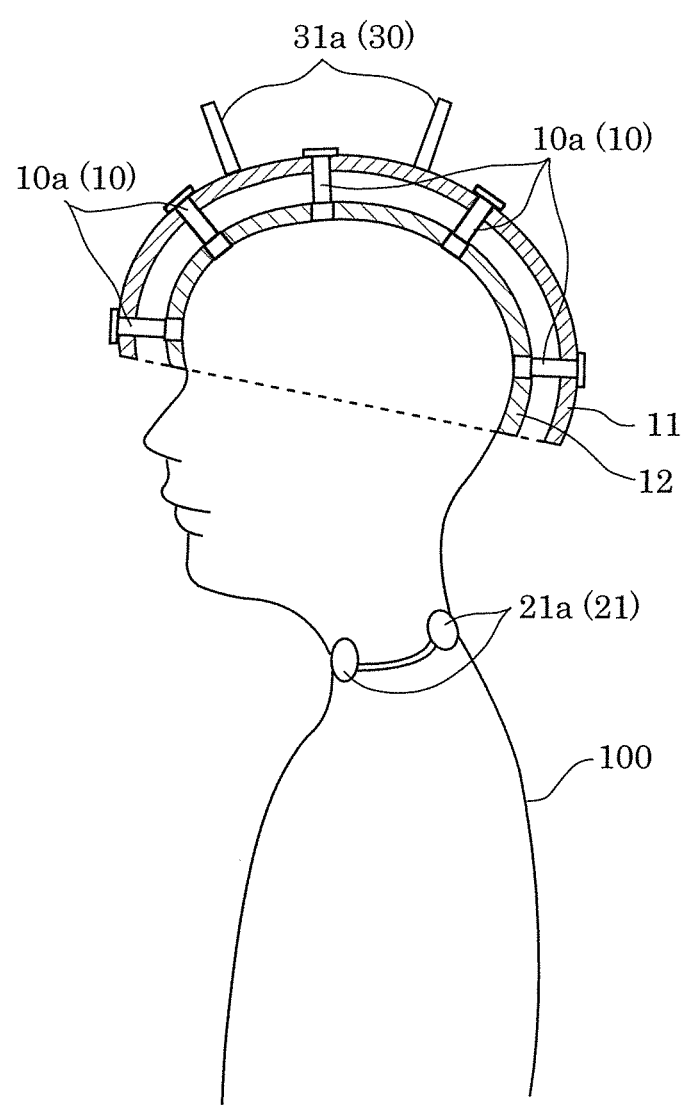
FIG. 2 is an illustration schematically depicting the manner in which a biological signal of a user is measured using the biological signal measurement system according to Embodiment 1.
Figures 3, 4:
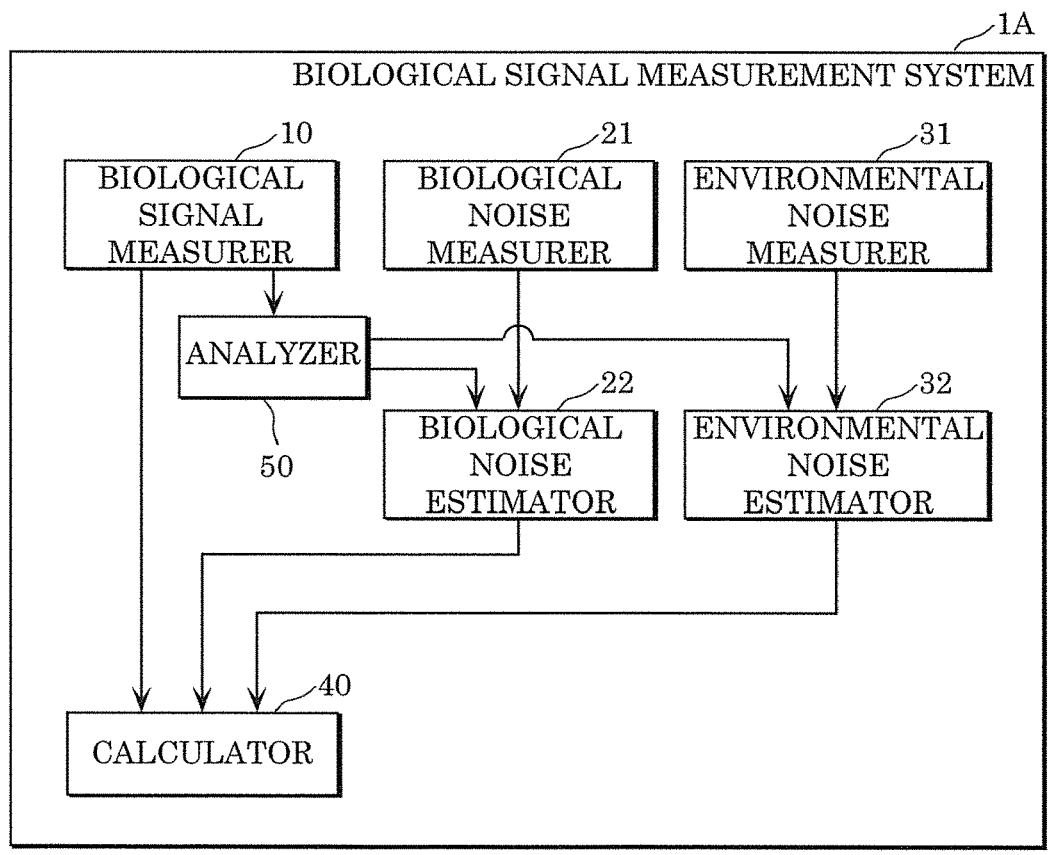
FIG. 3 is a table illustrating examples of signals which are measured using the biological signal measurement system according to Embodiment 1.
FIG. 4 is a block diagram illustrating the configuration of a biological signal measurement system according to a modification of Embodiment 1.

First, biological signal measurement system 1 according to Embodiment 1 will be described using FIG. 1 to FIG. 3. FIG. 1 is a block diagram illustrating the configuration of biological signal measurement system 1 according to Embodiment 1. FIG. 2 is an illustration schematically depicting the manner in which a biological signal of user 100 is measured using biological signal measurement system 1. FIG. 3 is a table illustrating examples of signals which are measured using biological signal measurement system 1.

As illustrated in FIG. 1, biological signal measurement system 1 in this embodiment includes biological signal measurer 10, biological noise measurer 21, biological noise estimator 22, environmental noise measurer 31, environmental noise estimator 32, and calculator 40.

Biological signal measurement system 1 is a system that measures a biological signal related to a living body like a human, such as brain waves, pulsation, cardiac beat, electrocardiogram, breathing, perspiration, a temperature at a portion or a blood flow volume, and thereby analyzes biological information on the living body. As illustrated in FIG. 3, in this embodiment, the target piece of biological information to be measured is brain waves including no noise. For instance, as illustrated in FIG. 2, the brain waves of user (subject) 100 are measured as a biological signal.

Biological signal measurer 10 is a device, for instance, for measuring a target biological signal of user 100 to be measured. Biological signal measurer 10 measures a biological signal including external noise of biological noise and of environmental noise. The biological noise and the environmental noise included in the biological signal measured by biological signal measurer 10 may be zero in some cases. In other words, in the biological signal of user 100 measured by biological signal measurer 10, the external noise of the biological noise and of the environmental noise is included as zero (in short, no external noise is included) in some cases.

When brain waves are measured as a biological signal as in this embodiment, for instance, biological signal measurer 10 may have a configuration that uses electrodes 10a attachable to the head of user 100 as illustrated in FIG. 2. For instance, biological signal measurer 10 has a plurality of electrodes 10a mounted on fixing tool 11 so that electrodes 10a come into contact with a scalp, and measures a potential difference between the plurality of electrodes 10a, thereby measuring the brain waves of user 100. On the measured brain waves, the external noise of the biological noise and of the environmental noise is superimposed.

It is to be noted that fixing tool 11 is, for instance, a helmet or the like to be attached to the head of user 100. As illustrated in FIG. 2, insulator 12 composed of an insulating rubber or the like is provided in fixing tool 11 so as to cover the head and come into contact with the scalp.

The external noise included in the biological signal measured is noise component other than the target biological signal to be measured. The external noise includes biological noise which is originating from a living body, and environmental noise which is not originating from a living body.

In this embodiment, the biological noise is the noise originating from a user 100 when a biological signal is measured by the biological signal measurer 10. For instance, the biological noise is noise originating from a myoelectric potential of a living body. On the other hand, the environmental noise is noise which is not originated from user 100 when a biological signal is measured by biological signal measurer 10. For instance, the environmental noise is noise which is originated from a factor such as peripheral equipment or a temperature in measurement environment.

Biological noise measurer 21 measures a signal which includes biological noise. When brain waves are measured as biological signal, biological noise measurer 21 may have a configuration that uses electrodes 21a attachable to the vicinity of at least one of the throat, an eye, and a temple of user 100. In this embodiment, biological noise measurer 21 has a plurality of electrodes 21a which are attached so as to come into contact with the throat of user 100, and measures a potential difference between the plurality of electrodes 21a, thereby measuring biological noise which is originated from a myoelectric potential of user 100 (living body) and occurs when user 100 grinds the tooth, when user 100 swallows spit or when user 100 moves the head.

It is to be noted that for a biological signal measured by biological signal measurer 10, each electrode 21a may be disposed in the vicinity of a portion (a source of biological noise) where biological noise is more likely to occur. For this reason, in this embodiment, in order to measure biological noise originating from a myoelectric potential when user 100 grinds the tooth, electrode 21a may be disposed in the vicinity of the throat of user 100, for instance. Also, it is possible to measure biological noise originating from a myoelectric potential when user 100 grinds the tooth by disposing electrode 21a in the vicinity of a temple of user 100. In addition, it is possible to measure biological noise originating from a myoelectric potential when user 100 blinks by disposing electrode 21a in the vicinity of an eye of user 100.

Biological noise estimator 22 estimates biological noise from the signal measured by biological noise measurer 21. In this embodiment, biological noise estimator 22 estimates the biological noise to be a first signal (b×B) which is obtained by multiplying the signal (B) measured by biological noise measurer 21 by a first constant (b).

Environmental noise measurer 31 measures a signal which includes environmental noise. When brain waves are measured as a biological signal as in this embodiment, environmental noise measurer 31 measures environmental noise originating from magnetism and radio waves generated by peripheral equipment (such as a lighting device, an AC adapter) present in the environment of brain wave measurement. For instance, as illustrated in FIG. 2, environmental noise measurer 31 may have a configuration that uses electrodes 31a attachable to the head of user 100. In this embodiment, environmental noise measurer 31 has a plurality of electrodes 31a mounted on fixing tool 11 so that electrodes 31a come into no contact with the scalp, and measures a potential difference between the plurality of electrodes 31a, thereby measuring environmental noise. Electrodes 31a are formed so as not to come into contact with the scalp by insulator 12 provided in fixing tool 11, and thus are electrically separated from Electrode 21a and the living body.

It is to be noted that environmental noise measurer 31 may measure the environmental noise at a portion near user 100 (living body). Thus, for a biological signal measured by biological signal measurer 10, electrodes 31a may be disposed in the vicinity of a portion (a source of environmental noise) where environmental noise is more likely to occur. For instance, electrodes 31a may be disposed at a portion near electrodes 10a.

Environmental noise estimator 32 estimates environmental noise from the signal measured by environmental noise measurer 31. In this embodiment, environmental noise estimator 32 estimates the environmental noise to be a second signal ($c \times C$) which is obtained by multiplying the signal ($C$) measured by environmental noise measurer 31 by a second constant ($c$).

Calculator 40 calculates a biological signal in consideration of the effect of the external noise of the biological noise and of the environmental noise using the signal measured by biological signal measurer 10, the biological noise estimated by biological noise estimator 22 and the environmental noise estimated by environmental noise estimator 32.

In this embodiment, calculator 40 calculates a biological signal in consideration of the effect of the external noise by subtracting the first signal ($b \times B$) which is the biological noise estimated by biological noise estimator 22 and the second signal ($c \times C$) which is the environmental noise estimated by environmental noise estimator 32 from signal ($A$) measured by biological signal measurer 10.

In this manner, in this embodiment, the external noise of the biological noise and of the environmental noise is removed from the biological signal measured by biological signal measurer 10 by a removal method using subtraction. Specifically, the biological noise and the environmental noise are estimated to be a certain number of times a signal including the biological noise measured by biological noise measurer 21 and a signal including the environmental noise measured by environmental noise measurer 31, and the estimated biological noise and environmental noise are removed from the biological signal measured by biological signal measurer 10.

Specifically, let $A$ be the biological signal measured by biological signal measurer 10, $B$ be the signal including the biological noise measured by biological noise measurer 21, and $C$ be the signal including the environmental noise measured by environmental noise measurer 31, then the biological noise is estimated to be $b \times B$ using the first constant $b$ and the environmental noise is estimated to be $c \times C$ using the second constant $c$, and biological signal $X$ is derived from the following (Expressions 1).

$$\text{Biological signal } X = A - b \times B - c \times C \qquad \text{(Expression 1)}$$

In this embodiment, biological signal $X$ is calculated as needed in real time. It is to be noted that a frequency filter may be pre-applied to the value of each signal measured by biological signal measurer 10, biological noise measurer 21 and environmental noise measurer 31. For instance, environmental noise with 50 Hz or higher coming from a fluorescent lamp or the like may be pre-removed by a frequency filter.

As described above, biological signal measurement system 1 in this embodiment includes: a biological signal measurer 10 that measures a biological signal including external noise of biological noise and of environmental noise; biological noise measurer 21 that measures a signal including the biological noise; biological noise estimator 22 that estimates the biological noise from signal measured by biological noise measurer 21; environmental noise measurer 31 that measures a signal including the environmental noise; environmental noise estimator 32 that estimates the environmental noise from the signal measured by environmental noise measurer 31; and calculator 40 that calculates the biological signal in consideration of the effect of the external noise using the signal measured by biological signal measurer 10, the biological noise estimated by biological noise estimator 22 and the environmental noise estimated by environmental noise estimator 32.

In this manner, in this embodiment, the biological signal excluding the external noise is obtained by removing the estimated biological noise and environmental noise from the signal measured by biological signal measurer 10. Consequently, it is possible to obtain a biological signal with a high S/N ratio in consideration of the effect of the external noise of the biological noise and of the environmental noise.

Also, in this embodiment, biological noise estimator 22 estimates the biological noise to be the first signal ($b \times B$) which is obtained by multiplying the signal ($B$) measured by biological noise measurer 21 by the first constant ($b$), and environmental noise estimator 32 estimates the environmental noise to be the second signal ($c \times C$) which is obtained by multiplying the signal ($C$) measured by environmental noise measurer 31 by the second constant ($c$). Then calculator 40 calculates a biological signal in consideration of the effect of the external noise by subtracting the first signal ($b \times B$) estimated by biological noise estimator 22 and the second signal ($c \times C$) estimated by environmental noise estimator 32 from signal ($A$) measured by biological signal measurer 10.

Thus, a biological signal excluding the external noise can be obtained by a removal method using subtraction. Therefore, it is possible to obtain a biological signal with a high S/N ratio, excluding the external noise.

Modification of Embodiment 1

Next, biological signal measurement system 1A according to a modification of Embodiment 1 will be described using FIG. 4. FIG. 4 is a block diagram illustrating the configuration of biological signal measurement system 1A according to a modification of Embodiment 1.

Biological signal measurement system 1A in this modification and biological signal measurement system 1 in Embodiment 1 differ in the method of removing the external noise from the biological signal measured by biological signal measurer 10.

Specifically, in biological signal measurement system 1 in Embodiment 1, the biological signal excluding the external noise is obtained by the removal method using subtraction, whereas in biological signal measurement system 1A in this modification, the biological signal excluding the external noise is obtained by independent component analysis. Specifically, in this modification, out of signals which are adapted to the signal measured by biological signal measurer 10 and are separated from biological signal measurer 10, a signal similar to each of the biological noise and the environmental noise is treated as external noise which is excluded from the biological signal measured by biological signal measurer 10. It is to be noted that similarly to Embodiment 1, in this modification, the target piece of biological information to be measured is brain waves.

As illustrated in FIG. 4, in addition to biological signal measurement system 1 of Embodiment 1 illustrated in FIG. 1, biological signal measurement system 1A in this modification includes analyzer 50 that performs the independent component analysis on the signal measured by biological signal measurer 10.

In this modification, biological noise estimator 22 estimates the biological noise to be an independent component similar to the signal measured by biological noise measurer 21 out of independent components as a result of signal separation by analyzer 50.

In addition, environmental noise estimator 32 estimates the environmental noise to be an independent component similar to the signal measured by environmental noise measurer 31 out of independent components as a result of signal separation by analyzer 50.

Then calculator 40 removes the biological noise estimated by biological noise estimator 22 and the environmental noise estimated by environmental noise estimator 32 from the signal measured by biological signal measurer 10, then calculates a biological signal excluding the biological noise and the environmental noise.

Figure 5:
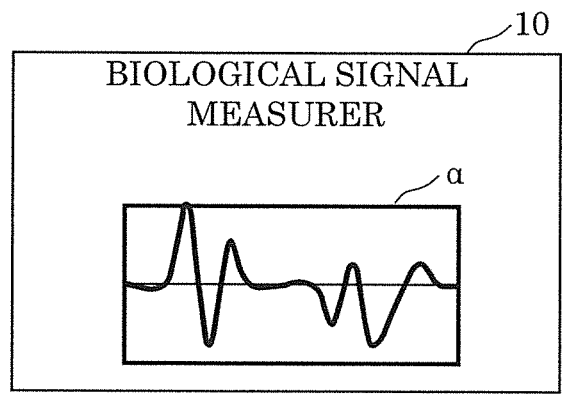
FIG. 5 is a graph illustrating an example of a signal measured by a biological signal measurer in the biological signal measurement system according to the modification of Embodiment 1.
Figure 6:
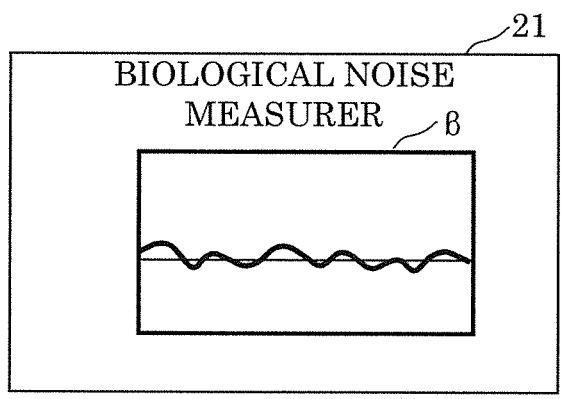
FIG. 6 is a graph illustrating an example of a signal measured by a biological noise measurer in the biological signal measurement system according to the modification of Embodiment 1.
Figure 7:
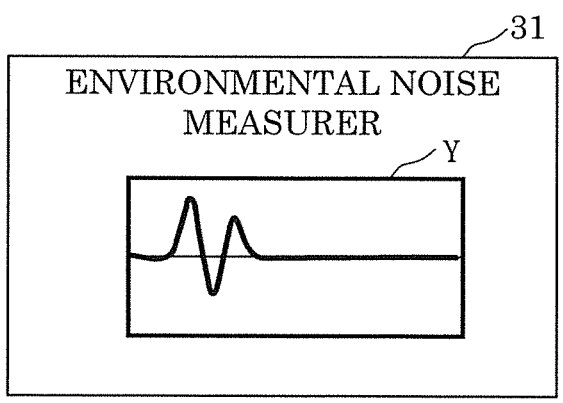
FIG. 7 is a graph illustrating an example of a signal measured by an environmental noise measurer in the biological signal measurement system according to the modification of Embodiment 1.
Figure 8:
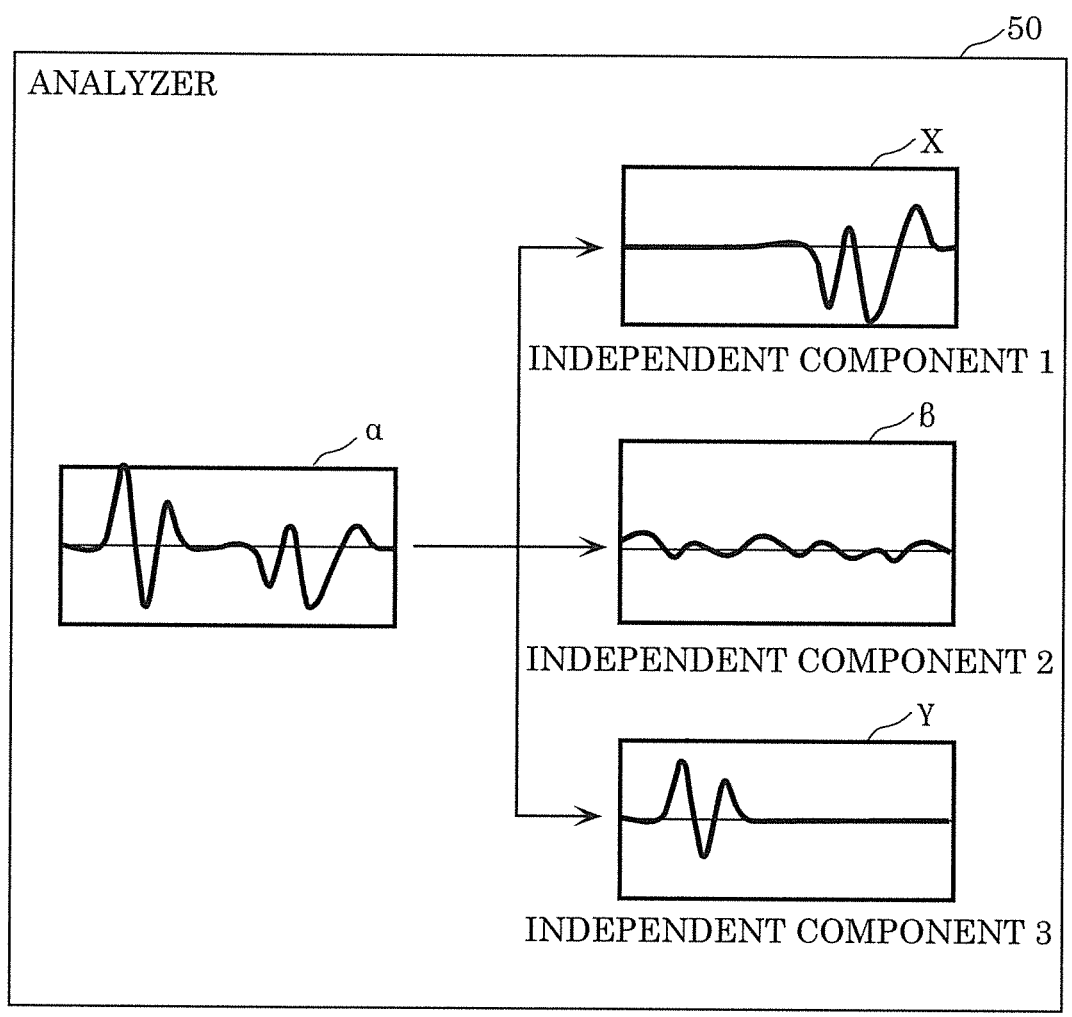
FIG. 8 illustrates graphs for explaining the operation of an analyzer in the biological signal measurement system according to the modification of Embodiment 1.

Here, a specific method of measuring a biological signal using biological signal measurement system 1A in this modification will be described using FIG. 5 to FIG. 8. FIG. 5 to FIG. 7 illustrate examples of respective signals measured by biological signal measurer 10, biological noise measurer 21 and environmental noise measurer 31 in biological signal measurement system 1A in this modification. FIG. 8 illustrates graphs for explaining the operation of analyzer 50 in biological signal measurement system 1A.

For instance, it is assumed that signal α with a waveform illustrated in FIG. 5 is measured by biological signal measurer 10, signal β with a waveform illustrated in FIG. 6 is measured by biological noise measurer 21, and signal γ with a waveform illustrated in FIG. 7 is measured by environmental noise measurer 31.

In this case, the independent component analysis is performed on signal α measured by biological signal measurer 10 by analyzer 50, and for instance, as illustrated in FIG. 8, signal α measured by biological signal measurer 10 is thereby separated into three signals: independent component 1, independent component 2, and independent component 3.

Based on the result of signal separation performed by analyzer 50, the biological noise and the environmental noise included in signal α measured by biological signal measurer 10 are estimated.

Specifically, in biological noise estimator 22, the result of signal separation by analyzer 50 is compared with signal β measured by biological noise measurer 21, and an independent component most similar to signal β measured by biological noise measurer 21 out of three independent components resulting from the signal separation by analyzer 50 is estimated to be the biological noise. In this modification, independent component 2 is the most similar to signal β measured by biological noise measurer 21 out of the three independent components: independent component 1, independent component 2, and independent component 3 illustrated in FIG. 8. Thus, it is estimated that independent component 2 is the biological noise.

Also, in environmental noise estimator 32, the result of signal separation by analyzer 50 is compared with signal γ measured by environmental noise measurer 31, and an independent component most similar to signal γ measured by environmental noise measurer 31 out of three independent components resulting from the signal separation by analyzer 50 is estimated to be the environmental noise. In this modification, independent component 3 is the most similar to the signal measured by environmental noise measurer 31 out of the three independent components: independent component 1, independent component 2, and independent component 3 illustrated in FIG. 8. Thus, it is estimated that independent component 3 is the environmental noise.

Consequently, out of the three independent components, independent component 1, independent component 2, and independent component 3 illustrated in FIG. 8, independent component 1 can be determined to be the target biological signal to be acquired, that is, biological signal X excluding the external noise of the biological noise and of the environmental noise.

The determination is made by calculation of calculator 40. Specifically, signal β of the biological noise estimated by biological noise estimator 22 and signal γ of the environmental noise estimated by environmental noise estimator 32 are removed from signal α measured by biological signal measurer 10 by calculator 40, and biological signal X is thereby derived.

It is to be noted that in this modification, when signal α, signal β and signal γ are compared to each other, the values of the signals at a certain point are not compared, but the waveforms of the signals in a certain range are compared. Therefore, in this modification, for signal α, signal β and signal γ, it is necessary to obtain signals (waveform signals) in a predetermined time range by biological signal measurer 10, biological noise measurer 21 and environmental noise measurer 31.

As described above, similarly to Embodiment 1, biological signal measurement system 1A in this modification includes biological signal measurer 10, biological noise measurer 21, biological noise estimator 22, environmental noise measurer 31, environmental noise estimator 32 and calculator 40. Calculator 40 calculates a biological signal in consideration of the effect of the external noise of the biological noise and of the environmental noise using the signal measured by biological signal measurer 10, the biological noise estimated by biological noise estimator 22, and the environmental noise estimated by environmental noise estimator 32.

In this manner, similarly to Embodiment 1, in this modification, the estimated biological noise and environmental noise are excluded from the signal measured by biological signal measurer 10, and thus the biological signal excluding the external noise is obtained. Thus, it is possible to obtain a biological signal with a high S/N ratio in consideration of the effect of the external noise of the biological noise and of the environmental noise.

Also, in this modification, analyzer 50 is provided that performs the independent component analysis of the signal measured by biological signal measurer 10. Biological noise estimator 22 then estimates the biological noise to be an independent component similar to the signal measured by biological noise measurer 21 out of independent components as a result of signal separation by analyzer 50. In addition, environmental noise estimator 32 estimates the environmental noise to be an independent component similar to the signal measured by environmental noise measurer 31 out of independent components as a result of signal separation by analyzer 50. Furthermore, calculator 40 removes estimated biological noise and environmental noise from the signal measured by biological signal measurer 10, then calculates a biological signal excluding the biological noise and the environmental noise.

Thus, a biological signal excluding the external noise can be obtained by the independent component analysis. Therefore, it is possible to obtain a biological signal with a high S/N ratio, excluding the external noise.

Embodiment 2

Figure 9:
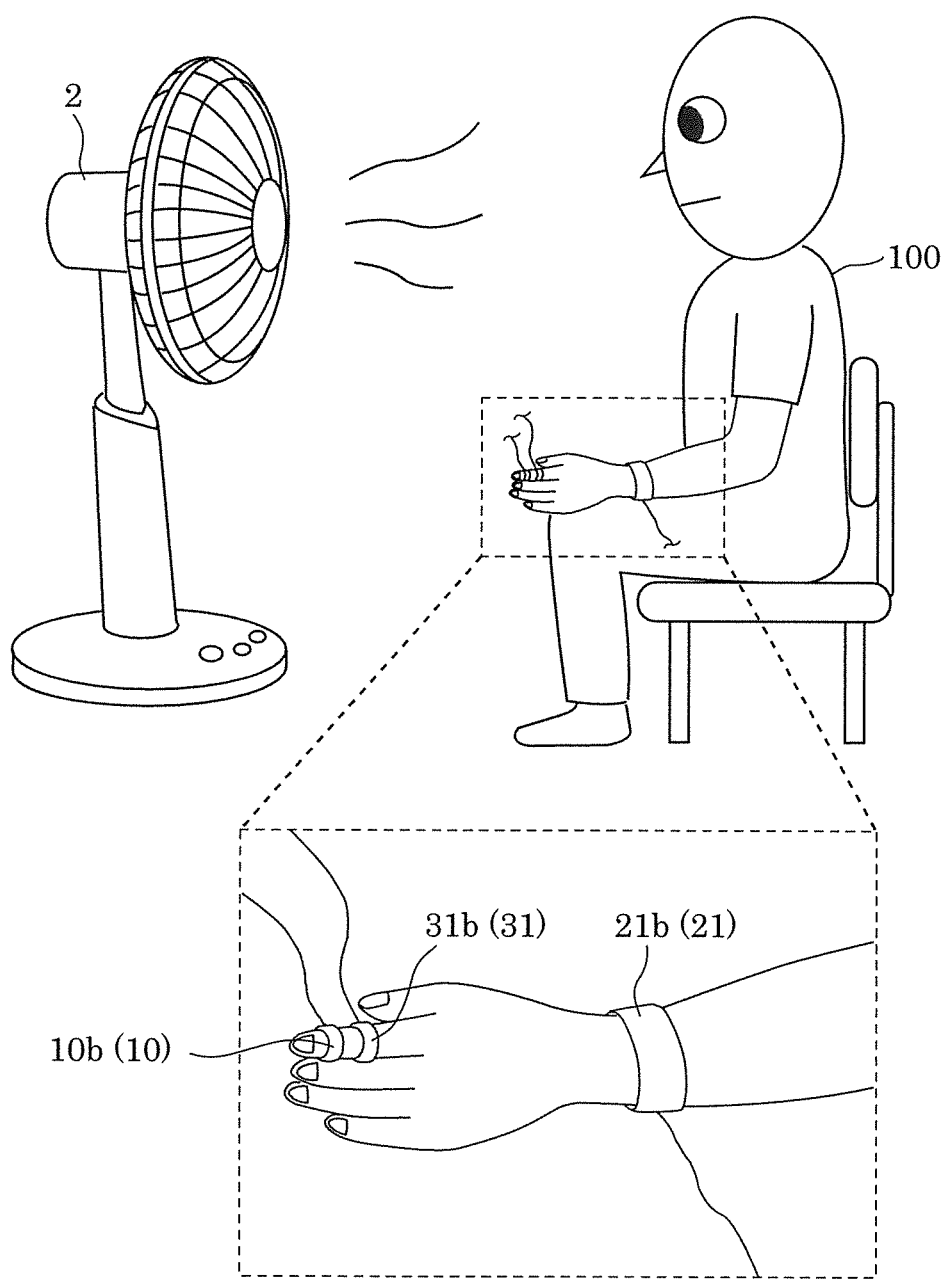
FIG. 9 is an illustration schematically depicting the manner in which a biological signal of a user is measured using a biological signal measurement system according to Embodiment 2.

Next, a biological signal measurement system according to Embodiment 2 will be described using FIG. 9 and FIG. 10. FIG. 9 is an illustration schematically depicting the manner in which a biological signal of user 100 is measured using the biological signal measurement system according to Embodiment 2. FIG. 10 is a table illustrating examples of signals measured by using the biological signal measurement system.

The configuration of the biological signal measurement system in this embodiment is the same as the configuration of the biological signal measurement system in Embodiment 1 and modification. For instance, in this embodiment, similarly to Embodiment 1 and modification, each technique of the removal method using subtraction and the independent component analysis can be used. Therefore, the configuration of the biological signal measurement system in this embodiment is the same as the configuration of biological signal measurement systems 1 and 1A illustrated in FIG. 1 and FIG. 4, for instance.

In this embodiment and Embodiment 1, target pieces of biological information to be measured are different. Specifically, the target piece of biological information to be measured is brain waves in Embodiment 1. However, in this embodiment, as illustrated in FIG. 10, the target piece of biological information to be measured is sympathetic nerve activity and parasympathetic nerve activity. Specifically, as illustrated in FIG. 9, the biological signal measurement system in this embodiment has a purpose of quantifying the stress (lassitude) of user 100 when receiving the wind of electric fan 2, and measures the activity of the sympathetic nerve and the parasympathetic nerve of user 100.

In this case, in general, it is believed that the temperature of a hand fingertip reflects the sympathetic nerve activity and parasympathetic nerve activity, and thus the sympathetic nerve activity and parasympathetic nerve activity can be measured by measuring the temperature of a hand fingertip.

However, the temperature of a fingertip is also affected by the biological noise and the environmental noise. These biological noise and environmental noise affect the temperature of a fingertip as external noise. For instance, the temperature of a wrist and the temperature of the back of a hand affect the temperature of a fingertip as biological noise. In addition, the temperature, humidity, air current (wind speed) and radiant heat affect the temperature of a fingertip as environmental noise.

Thus, similarly to Embodiment 1, in this embodiment, biological signal of user 100 is measured as well as the biological noise and the environmental noise are measured, and thus only the biological signal with the external noise removed is obtained.

Specifically, when the temperature of a hand fingertip is measured as a biological signal, biological signal measurer 10 may be attachable to a hand fingertip of user 100. For instance, as illustrated in FIG. 9, biological signal measurer 10 has thermometer 10b attachable to a hand fingertip of user 100, and the temperature of a hand fingertip of user 100 is measured by thermometer 10b.

In this case, biological noise measurer 21 may be attachable to at least one of a wrist and the back of a hand of user 100. For instance, as illustrated in FIG. 9, biological noise measurer 21 has thermometer 21b attachable to a wrist of user 100, and the temperature of a wrist of user 100 is measured by thermometer 21b. It is to be noted that biological noise measurer 21 is not limited to be attachable to a wrist and the back of a hand of user 100, and may be attachable to a palm or a first joint of a finger.

As illustrated in FIG. 9, environmental noise measurer 31 has measuring instrument 31b attachable to a hand fingertip of user 100, and the temperature, humidity, air current and radiant heat are measured as environmental noise in the measurement environment by measuring instrument 31b. It is to be noted that environmental noise measurer 31 may not be attachable to a hand fingertip of user 100.

In this embodiment, biological noise estimator 22, environmental noise estimator 32 and calculator 40 are the same as those in Embodiment 1 and the modification. Specifically, biological noise estimator 22 estimates the biological noise from the signal measured by biological noise measurer 21, and environmental noise estimator 32 estimates the environmental noise from the signal measured by environmental noise measurer 31. Calculator 40 then calculates a biological signal in consideration of the effect of the external noise of the biological noise and of the environmental noise using the signal measured by biological signal measurer 10, the biological noise estimated by biological noise estimator 22, and the environmental noise estimated by environmental noise estimator 32.

In this embodiment, when the sympathetic nerve activity and the parasympathetic nerve activity are measured, the biological signal to be measured by biological signal measurer 10 is a signal related to the temperature of a hand fingertip. However, without being limited to this, the biological signal to be measured by biological signal measurer 10 may be, for instance, the temperature of the nose, an instep or a foot fingertip as illustrated in FIG. 10. The sympathetic nerve activity and the parasympathetic nerve activity can be measured by the temperature of the nose, an instep or a foot fingertip. In this case, a portion at which the temperature is measured by biological noise measurer 21 can be selected as needed according to a portion at which a biological signal is measured as illustrated by the combinations of A to D of FIG. 10. Specifically, biological noise measurer 21 may be attachable to at least one of an ankle, an instep and the forehead of user 100.

As described above, similarly to Embodiment 1, in the biological-signal measurement system in this embodiment, the estimated biological noise and environmental noise are excluded from the signal measured by biological signal measurer 10, and thus the biological signal excluding the external noise is obtained. Thus, it is possible to obtain a biological signal with a high S/N ratio in consideration of the effect of the external noise of the biological noise and of the environmental noise.

Particularly, in this embodiment, the sympathetic nerve activity and the parasympathetic nerve activity in relation to wind can be measured with high accuracy.

Embodiment 3

Next, a biological signal measurement system according to Embodiment 3 will be described using FIG. 11 and FIG. 12. FIG. 11 is an illustration schematically depicting the manner in which a biological signal of user 100 is measured using the biological signal measurement system according to Embodiment 3. FIG. 12 is a table illustrating examples of signals measured by using the biological signal measurement system.

The configuration of the biological signal measurement system in this embodiment is the same as the configuration of the biological signal measurement system in Embodiment 1 and the modification. For instance, also in this embodiment, similarly to Embodiment 1 and the modification, each technique of the removal method using subtraction and the independent component analysis can be used. Therefore, the configuration of the biological signal measurement system in this embodiment is the same as the configuration of biological signal measurement systems 1 and 1A illustrated in FIG. 1 and FIG. 4, for instance.

In this embodiment and Embodiment 1, target pieces of biological information to be measured are different. Specifically, the target piece of biological information to be measured is brain waves in Embodiment 1. However, in this embodiment, as illustrated in FIG. 12, the target piece of biological information to be measured is brain activity. This embodiment has a purpose of quantifying the brain activity by recognizing change in the cerebral blood flow by light using Near-infrared Spectroscopy (NIRS).

In this embodiment, as a biological signal, biological signal measurer 10 measures change (change in blood flow volume) in the absorbance of portion of attention by the NIRS. Specifically, as illustrated in FIG. 11, the head of user 100 is irradiated with near-infrared light, and change in the degree (absorbance) of absorption of near-infrared light is measured. A change in the absorbance can be measured by a measuring probe.

Also, as a biological noise, biological noise measurer 21 measures change (change in blood flow volume) in the absorbance of the whole brain by the NIRS. For instance, biological noise measurer 21 measures change in the absorbance of the whole brain from the arteries of the neck. In this case, the arterial area of the neck of user 100 is irradiated with near-infrared light, and change in the degree (absorbance) of absorption of near-infrared light is measured by a measuring probe.

Also, as environmental noise, environmental noise measurer 31 measures change in lighting of lighting device 3 in the measurement environment. In this case, as environmental noise, environmental noise measurer 31 may further measure change in the incidence angle of the measuring probe when change in the absorbance is measured by biological signal measurer 10 and biological noise measurer 21. That is, measurement of change in the incidence angle of the measuring probe allows change of the effect of the light received from lighting device 3 due to tilting of the head of user 100 to be measured.

In this embodiment, biological noise estimator 22, environmental noise estimator 32 and calculator 40 are the same as those in Embodiment 1. Specifically, biological noise estimator 22 estimates the biological noise from the signal measured by biological noise measurer 21, and environmental noise estimator 32 estimates the environmental noise from the signal measured by environmental noise measurer 31. Calculator 40 then calculates a biological signal in consideration of the effect of the external noise of the biological noise and of the environmental noise using the signal measured by biological signal measurer 10, the biological noise estimated by biological noise estimator 22, and the environmental noise estimated by environmental noise estimator 32.

As described above, similarly to Embodiment 1, in the biological-signal measurement system in this embodiment, the estimated biological noise and environmental noise are excluded from the signal measured by biological signal measurer 10, and thus the biological signal excluding the external noise is obtained. Thus, it is possible to obtain a biological signal with a high S/N ratio in consideration of the effect of the external noise of the biological noise and of the environmental noise.

Particularly, in this embodiment, brain activity can be measured with high accuracy by the NIRS.

Embodiment 4

Figures 13, 14:
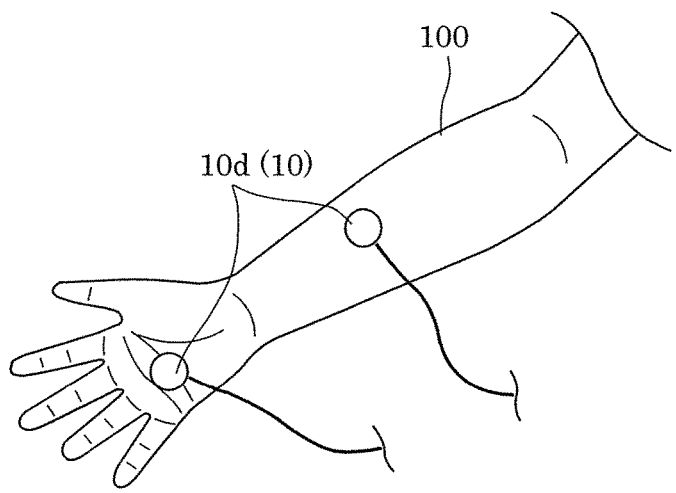
FIG. 13 is an illustration schematically depicting the manner in which a biological signal of a user is measured using a biological signal measurement system according to Embodiment 4.
FIG. 14 is a table illustrating examples of signals measured by using the biological signal measurement system according to Embodiment 4.

Next, the biological signal measurement system according to Embodiment 4 will be described using FIG. 13 and FIG. 14. FIG. 13 is an illustration schematically depicting the manner in which a biological signal of user 100 is measured using a biological signal measurement system according to Embodiment 4. FIG. 14 is a table illustrating examples of signals measured by using the biological signal measurement system according to Embodiment 4.

The configuration of the biological signal measurement system in this embodiment is the same as the configuration of the biological signal measurement system in Embodiment 1 and the modification. For instance, also in this embodiment, similarly to Embodiment 1 and the modification, each technique of the removal method using subtraction and the independent component analysis can be used. Therefore, the configuration of the biological signal measurement system in this embodiment is the same as the configuration of biological signal measurement systems 1 and 1A illustrated in FIG. 1 and FIG. 4, for instance.

In this embodiment and Embodiment 1, target pieces of biological information to be measured are different. Specifically, the target piece of biological information to be measured is brain waves in Embodiment 1. However, in this embodiment, as illustrated in FIG. 14, the target piece of biological information to be measured is emotional sweating. This embodiment has a purpose of quantifying the emotional sweating by identifying an amount of emotional sweating using a specific frequency.

In this embodiment, as a biological signal, biological signal measurer 10 measures a signal related to emotional sweating. Specifically, biological signal measurer 10 measures an amount of emotional sweating of user 100 by measuring a skin potential level (SPL). For instance, as illustrated in FIG. 13, biological signal measurer 10 has a plurality of electrodes 10d attachable to a palm and an arm of user 100, and measures a potential difference between the plurality of electrodes 10d, thereby measuring a skin potential level as an amount of emotional sweating of user 100.

Also, as biological noise, biological noise measurer 21 measures an amount of emotional sweating due to change in the body temperature of user 100. For instance, biological noise measurer 21 measures an amount of emotional sweating at the chest of user 100.

Also, as environmental noise, environmental noise measurer 31 measures the temperature, wind speed, and radiant heat in the measurement environment. For instance, biological noise measurer 21 measures the temperature, wind speed, and radiant heat by the same method as in Embodiment 2.

In this embodiment, biological noise estimator 22, environmental noise estimator 32 and calculator 40 are the same as those in Embodiment 1. Specifically, biological noise estimator 22 estimates the biological noise from the signal measured by biological noise measurer 21, and environmental noise estimator 32 estimates the environmental noise from the signal measured by environmental noise measurer 31. Calculator 40 then calculates a biological signal in consideration of the effect of the external noise of the biological noise and of the environmental noise using the signal measured by biological signal measurer 10, the biological noise estimated by biological noise estimator 22, and the environmental noise estimated by environmental noise estimator 32.

As described above, similarly to Embodiment 1, in the biological-signal measurement system in this embodiment, the estimated biological noise and environmental noise are excluded from the signal measured by biological signal measurer 10, and thus the biological signal excluding the external noise is obtained. Thus, it is possible to obtain a biological signal with a high S/N ratio in consideration of the effect of the external noise of the biological noise and of the environmental noise.

Particularly, in this embodiment, emotional sweating (SPL) can be measured with high accuracy.

Other Modifications

Although the biological signal measurement system according to the present disclosure has been described based on the embodiments and the modification in the above, the present disclosure is not limited to the embodiments and the modification.

For instance, embodiments obtained by making various modifications, which occur to those skilled in the art, to the embodiments and the modification, and an embodiment implemented in any combination of the components and functions of the embodiments and modification in a range without departing from the scope of the present disclosure are also included in the present disclosure.

In the embodiments, the processing described as the operations of the following components can be execute by a computer: biological signal measurer 10, biological noise measurer 21, biological noise estimator 22, environmental noise measurer 31, environmental noise estimator 32, calculator 40, and analyzer 50. For instance, a computer executes a program using a processor (CPU), hardware resources such as a memory and an input/output circuit, thereby performing the aforementioned processing. Specifically, a processor obtains target data for processing from a memory or an input/output circuit to calculate the data, and outputs a calculation result to a memory or an input/output circuit, thereby performing the processing.

A program for executing the aforementioned processing may be recorded on a non-transitory recording medium such as a computer-readable CD-ROM. In this case, a computer reads a program from a non-transitory recording medium, and performs each processing by executing the program.

It is to be noted that the present disclosure can be implemented as a program for causing a computer to function as the biological signal measurement system, or as a computer-readable recording medium in which the program is stored.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A biological signal measurement system comprising:
a processor;
a biological sensor configured to be attached on a body part of a living body configured to measure a biological signal that includes external noise of biological noise and of environmental noise, wherein the biological noise is noise originating from the living body, and the environmental noise is noise not originating from the living body;
a biological noise sensor configured to be attached on a second body part of the living body different from the first body part, and configured to measure a first noise signal including the biological noise while the biological signal is measured by the biological sensor, the first noise signal measured by the biological noise sensor not including the environmental noise;
and an environmental noise sensor configured to measure a second noise signal including the environmental noise, the second noise signal measured by the environmental noise sensor not including the biological noise;
wherein the processor is configured to:
estimate the biological noise from the first noise signal measured by the biological noise sensor;
estimate the environmental noise from the second noise signal measured by the environmental noise sensor; and
calculate a resultant biological signal as a function of the biological signal measured by the biological sensor, the estimated biological noise and the estimated environmental noise.

2. The biological signal measurement system according to claim 1,
wherein the processor estimates the biological noise to be a first estimated noise signal obtained by multiplying the first noise signal measured by the biological noise sensor by a first constant,
the processor estimates the environmental noise to be a second estimated noise signal obtained by multiplying the second noise signal measured by the environmental noise sensor by a second constant, and
the processor calculates the biological signal as a function of the estimated biological noise and the estimated environmental noise by subtracting the first estimated noise signal and the second estimated noise signal from the biological signal measured by the biological sensor.

3. The biological signal measurement system according to claim 1, further comprising an analyzer that performs independent component analysis of the biological signal measured by the biological sensor,
wherein the processor estimates the biological noise to be a first independent component most similar to the biological signal measured by the biological noise sensor out of at least one independent component as a result of signal separation by the analyzer, the processor estimates the environmental noise to be a second independent component most similar to the signal measured by the environmental noise sensor out of the at least one independent component as the result of signal separation by the analyzer, and the processor calculates the biological signal excluding the biological noise and the environmental noise by removing the estimated biological noise and the estimated environmental noise from the biological signal measured by the biological sensor.

4. The biological signal measurement system according to claim 1,
wherein the biological signal is brain waves,
the biological sensor has a first electrode attachable to a head of a user, and
the biological noise sensor has a second electrode attachable to a vicinity of at least one of a throat, an eye, and a temple of the user.

5. The biological signal measurement system according to claim 1,
wherein the biological signal is related to a temperature of at least one of a hand fingertip, the nose, an instep and a foot fingertip of a user,
the biological sensor is attachable to at least one of a hand fingertip, the nose, an instep and a foot fingertip of the user, and
the biological noise sensor is attachable to at least one of a wrist, a back of a hand, a palm, a first joint of a finger, a forehead, an ankle and an instep of the user.

6. The biological signal measurement system according to claim 1,
wherein the biological signal is related to a cerebral blood flow,
the biological sensor measures a first absorbance at a point of attention of a head of a user, and
the biological noise sensor measures a second absorbance of the whole brain of the user.

7. The biological signal measurement system according to claim 1,
wherein the biological signal is related to emotional sweating,
the biological sensor measures a first amount of sweat produced by a user due to emotional sweating, and
the biological noise sensor measures a second amount of sweat produced due to a change in body temperature of the user.

8. A biological signal measurement system comprising:
a processor;
a biological sensor configured to be attached on a first body part of a living body, the biological sensor being configured to measure a biological signal of a living body, the biological signal including biological noise and environmental noise, wherein the biological noise is noise originating from the living body, and the environmental noise is noise not originating from the living body;
a biological noise sensor configured to be attached on a second body part of the living body different from the first body part, the biological noise sensor being separate from the biological sensor, and configured to measure, based on the living body, the biological noise the biological signal is to generate a first noise signal including the biological noise; and
an environmental noise sensor, the environmental noise sensor being separate from the biological sensor, and configured to measure, independently of the living body, the environmental noise while the biological signal is measured by the biological sensor to generate a second noise signal including the environmental noise;
wherein the processor is configured to:
estimate the biological noise from the first noise signal measured by the biological noise sensor;
estimate the environmental noise from the second noise signal measured by the environmental noise sensor; and
calculate a resultant biological signal as a function of the biological signal measured by the biological sensor, the estimated biological noise and the estimated environmental noise.

9. The biological signal measurement system according to claim 8, wherein the environmental noise sensor measures at least one of magnetic or radio noise generated by peripheral equipment; a temperature; a humidity; an air current; a radiant heat; a change in lighting in measurement environment; a change in an incident angle to a measuring probe; and a wind speed.

10. The biological signal measurement system according to claim 8,
wherein the processor estimates the biological noise to be a first estimated noise signal obtained by multiplying the first noise signal measured by the biological noise sensor by a first constant,
the processor estimates the environmental noise to be a second estimated noise signal obtained by multiplying the second signal measured by the environmental noise sensor by a second constant, and
the processor calculates the biological signal as a function of the biological noise and the environmental noise by subtracting the first estimated noise signal and the estimated noise second signal from the biological signal measured by the biological sensor.

11. The biological signal measurement system according to claim 8,
wherein the biological signal is brain waves,
the biological sensor has a first electrode attachable to a head of a user, and
the biological noise sensor has a second electrode attachable to a vicinity of at least one of a throat, an eye, and a temple of the user.

12. The biological signal measurement system according to claim 8,
wherein the biological signal is related to a temperature of at least one of a hand fingertip, the nose, an instep and a foot fingertip of a user,
the biological sensor is attachable to at least one of a hand fingertip, the nose, an instep and a foot fingertip of the user, and
the biological noise sensor is attachable to at least one of a wrist, a back of a hand, a palm, a first joint of a finger, a forehead, an ankle and an instep of the user.

13. The biological signal measurement system according to claim 8,
wherein the biological signal is related to a cerebral blood flow,
the biological sensor measures a first absorbance at a point of attention of a head of a user, and
the biological noise sensor measures a second absorbance of the whole brain of the user.

14. The biological signal measurement system according to claim 8,
wherein the biological signal is related to emotional sweating,
the biological sensor measures a first amount of sweat produced by a user due to emotional sweating, and the biological noise sensor measures a second amount of sweat produced due to a change in body temperature of the user.

\* \* \* \* \*